United States Patent [19]

Welsh

[11] Patent Number: 4,545,370
[45] Date of Patent: Oct. 8, 1985

[54] KINETIC BACK SUPPORT BELT

[76] Inventor: Thomas M. Welsh, 9303 W. Parkhill Dr., Bethesda, Md. 20814

[21] Appl. No.: 532,221

[22] Filed: Sep. 14, 1983

[51] Int. Cl.$^4$ .......................... A61F 5/02; A61F 5/24; A41F 3/02
[52] U.S. Cl. ...................................... 128/78; 128/95; 2/321; 2/338
[58] Field of Search ....................... 128/78, 95, 69, 75, 128/133, 134; 2/338, 321, 322, 336

[56] References Cited

U.S. PATENT DOCUMENTS

| | | | |
|---|---|---|---|
| 253,952 | 2/1882 | Sternheimer | 2/322 |
| 648,267 | 4/1900 | Koch | 2/338 |
| 1,903,081 | 3/1933 | Wotherspoon | 2/338 X |
| 2,681,453 | 6/1954 | Lane | 2/322 |
| 3,052,236 | 9/1962 | Schrieber | 128/78 |
| 3,096,760 | 7/1963 | Nelkin | 128/95 |
| 3,097,640 | 7/1963 | Morgan | 128/78 |
| 3,587,570 | 6/1971 | Kilbey | 128/75 |
| 4,348,774 | 9/1982 | Woodson | 2/338 |

FOREIGN PATENT DOCUMENTS 7605947 3/1976 France ................... 128/78

OTHER PUBLICATIONS

Joe Weider's "Muscle & Fitness", Mar. 1983, p. 232.
Rene Cailliet, M.D., "Low Back Pain Syndrome", Ed. 3, pp. 126–128, (1982).
D. L. Bartelink, "The Role of Abdominal Pressure in Relieving the Pressure on the Lumbar Intervertebral Discs", pp. 716–725, (1957).
J. M. Morris et al., "The Journal of Bone and Joint Surgery", vol. 43A, No. 3, pp. 327–351, (1961).
Paul L. Norton et al., "The Immobilizing Efficiency of Back Braces", vol. 39A, No. 1, pp. 111–139, (1957).
Time Magazine, "That Aching Back!", pp. 30–38, (1980).
Allen S. Russek, "Orthopaedic Review", vol. V, No. 4, pp. 21–31, (1976).
Beth Melton, "Occupational Health and Safety", pp. 20–23, (1983).
G. E. Miller Catalog 100, Physical Rehabilitation Equipment, 1984.

Primary Examiner—Richard J. Apley
Assistant Examiner—Alan W. Cannon
Attorney, Agent, or Firm—Birch, Stewart, Kolasch & Birch

[57] ABSTRACT

A back support belt formed of a relatively rigid material having a width of 3½ to 6 inches and a method of limiting the movement of a person in preventing lower back injury are disclosed. The belt reduces risk of lower back injury by restricting movement of the wearer, applying bio-mechanical directed forces to specific areas of the midsection and lateral trunk of the wearer and by utilizing pressure points which remind the wearer to use proper lifting techniques and good body mechanics.

21 Claims, 5 Drawing Figures

KINETIC BACK SUPPORT BELT

BACKGROUND AND SUMMARY OF THE INVENTION

The present invention relates to a method for reducing the injury to the lower back from biomechanical and overfatigue stress and an improved belt which is particularly useful in the method for reducing the risk of injury to the lower back.

Lower back pain is largely a social and fitness problem. It can be caused by a traumatic injury or can be caused by the general lifestyle of an individual. The kinetic back support belt is a device for accommodating and alleviating this situation. The belt is designed to be used to increase the effectiveness of the abdominal wall in elevating intracavity pressure, in restricting abnormal and stressful trunk motion, in improving skeletal alignment, and in continually training a wearer thereof in proper body mechanics of lifting, stooping, and bending. All of these factors are recommended as contributory factors to a healthy back.

Numerous patents and articles have described devices seeking to achieve one or more of the above aims. However, these devices are not usually useful by a person for the performance of everyday tasks for the protection and reinforced training for persons with or without prior back injury. The kinetic belt can be used by warehouse materials handlers, carpenters, truck mechanics, post-partem mothers, policemen, nurses, meat cutters and homeowners. It may be worn over any clothing at home or at work as a protective device when performing occassional or frequent activities that potentially may sprain the musculo-skeletal structures of the lumbarsacral area. It has been found convenient to use on and off during activities of daily living.

The back support belt is formed of a material having a sufficient rigidity and flexibility and an appropriate size so that when it is properly applied to a user, it creates medically directed forces and pressure points which protect the lower back and prevent injury. The belt is specially designed to contact specific points in the skeletal structure and to increase the intracavity abdominal pressure of the wearer. By increasing this pressure, forces are generated within the abdominal cavity which press against the anterior portion of the lower back and spine. The belt when properly applied, also limits forward, backward and lateral movement of the trunk. In addition to physically limiting or restricting the movement of a wearer, the belt also exerts pressure at specific pressure points when a wearer attempts to bend or move in a direction which could possibly cause back injury. These pressure areas or pressure points act as a form of biofeedback reminding the wearer of allowable and safe limits of trunk flexion and rotation.

In a preferred embodiment, the back support belt comprises an elongate support band having a first and second longitudinal end. The support band is preferably formed of a relatively rigid contiguous material which is rigid enough to maintain its shape during wear and to exert pressure at selected pressure points during wear and at the same time is also flexible enough to be wrapped around a wearer's body and conform to the general contours of the wearer's body. The support band is preferably formed of leather which is 4–8 mm thick, preferably $4\frac{3}{4}$ to 7 mm thick. However, other materials having similar rigidity and flexibility as leather can also be substituted for leather. The support band is $3\frac{1}{2}$ to 6 inches wide, preferably $3\frac{3}{4}$ to $5\frac{1}{2}$ inches wide, depending upon the height of the individual. The support band is preferably longer than the waist measurement of the wearer, preferably 5 to 11 inches longer than the waist measurement of the wearer and more preferably 6 to 10 inches longer than the waist measurement of the wearer. This overlap length will vary according to pelvic width and the distance between the medical aspects of the anterior superior iliac spines.

The back support belt also comprises means for tightening the belt around a subject. This tightening means is preferably arranged on the belt in a position wherein when the tightening means is connected, the first and second longitudinal ends of the support band overlap the desired distance. The tightening means is also preferably arranged in a manner so that the tightening means applies pressure to both of the overlapped longitudinal ends of the belt to provide for increased intraabdominal pressure.

The back support belt is preferably formed of an elongate support band formed of a single piece of leather having a substantially uniform width along the entire length thereof. Although it is not absolutely necessary that the belt has a substantially uniform width along the entire length thereof, it is important that the belt, especially in the front and sides thereof, has a width sufficient to apply maximum intraabdominal pressure and prevent forward and lateral bending of the wearer. Another advantage obtained by using a belt having a relatively wide front portion is that when the belt presses against the abdomen, it forces the chest cavity and upper body of the wearer slightly upward thereby relieving inter-disc pressure in the spine.

The tightening means for the back support belt preferably includes a first tightening strap connected with one longitudinal end of the support band and means for adjustably fastening the tightening strap to the elongate support band. The back support belt may also include a second tightening strap connected with the other longitudinal end of the support band which cooperates with said first tightening strap to tighten the support band on the wearer. The first and second tightening straps can be formed of a variety of materials. However, the tightening straps are usually formed of a material which is more flexible than the support band for ease of manipulation. The first and second tightening straps preferably have a width smaller than the width of the support band. If a buckle is utilized to connect the first and second tightening straps, the buckle preferably has a width smaller than the width of said support band whereby the buckle does not discomfort the wearer during forward flexion of the trunk.

In a preferred embodiment the back support belt consists essentially of a $3\frac{1}{2}$ to 6 inch wide elongate support band having first and second longitudinal ends, said support band being formed of leather which is 4–8 mm thick or being formed of a relatively stiff material having a similar stiffness and flexibility as said leather and tightening means for tightening said belt around the midsection of a subject in a position wherein said first and second longitudinal ends of said support belt overlap between 6 to 10 inches and further wherein said tightening means urges both of said overlapping longitudinal ends of said belt against the abdomen of a subject when being worn.

Because of its unique two-piece design, the kinetic back support belt can be adapted to various work situations by attaching accessories directly to the more rigid wider straps of the support band in the front, back and/or sides thereof without interfering with the more flexible narrow tightening or connecting straps and buckle fastener. Examples of attachments are snaps and loops for tools, safety devices, pockets for carrying, and handle grips on nurses belts for patients to grasp while being lifted from chair to chair.

One of the features that differentiates the preferred embodiment of the belt from other belts is the overlapping front section. Anteriorly, the double thickness in the overlapping front section assists weak abdominal muscles, particularly the rectus abdominis, and provides a posteriorly directed force to increase intraabdominal pressure which has been shown to give longitudinal support to the spine and help control excessive lordosis of the lumbar spine. This is a condition that can arise from overfatigue and back strain. An abdominal pad may be attached to the underflap on the stomach side for even more abdominal pressure. Through pressure points of the sternal half of the tenth rib and the anterior portion of the iliac crest, excessive forward bending is restricted and the user is made aware of safe limits. The upper and lower edges of the sides of the belt are preferably not padded so that the pressure at the pressure points can be felt by the wearer.

Laterally, the edges of the belt band extend distally from the anterior border of the lateral portion of the tenth rib to the iliac crest. This distance varies from $3\frac{1}{2}$ to 6 inches depending upon the height of the individual. When the belt is tightened, a medically directed force is provided which may slightly limit lateral trunk motions occurring in the thoraco lumbar and lumbar areas. The pressure areas along the inferior border of the tenth rib and the superior border of the iliac crest act as a form of biofeedback reminding the wearer of allowable and safe limits of trunk lateral flexion and rotation. This is perhaps the most hazardous position of spinal mechanics that may lead to a back injury. Preferably, the upper and lower edges of the sides of the belt are not padded so that the pressure at the pressure points can be felt by the wearer.

Posteriorly, the edges of the belt band extend distally from about the thoraco lumbar joint to about the fifth lumbar joint. This provides for anteriorly directed forces which may limit excessive extension of the lumbar spine and thereby decrease lordosis. The pressure areas of the inferior edge of the dorsal portion of the tenth rib and the sacral iliac line of the ilium serve as reminding feedback when excessive extension of the spine is attempted. There is sufficient clearance between the strap and the lumbar spinous processes so as to allow for reduction of lordosis when the intra-abdominal pressure is increased by tightening the belt. This is also especially significant in preventing premature lumbar lordosis when assuming an erect posture from a forward flexed position. Preferably, the back of the belt is not provided with a pad in order to provide sufficient clearance between the support band and the spinous processes. Because of premature lumbar lordosis, the spine is eccentrically loaded and muscular action is needed to maintain it in this off-center balance. This position is inefficient, fatiguing and possibly injurious.

In regards to improving skeletal alignment and continually training the user in proper techniques of body mechanics, the belt of the present invention should be most helpful. Most people wearing a support will voluntarily restrict motion to a great extent because it is either a psychological or a physical reminder. A mildly restricting circumferential device can divert the forces from a particular ligament, relieve any single muscle from bearing the brunt of the force in a particular position, reinforce abdominal muscles and by its very presence and pressures create a set of reflexes of its own which can alter the effect of the underlying reflex reactions. Thus, reeducation and training is achieved by use of the belt of the present invention and the level of awareness to protect the back from injury is raised. This can be achieved if the belt is either tightened for a particular heavy task or loosened in performance of routine activities.

The present invention, in addition to being directed to a novel belt, is also directed to a novel method for limiting the movement of a person and preventing lower back injury. In a broad aspect, the method involves the steps of applying to a person to be treated a back support belt formed of a relatively rigid material and positioning and tightening the belt on the person to increase abdominal pressure and to apply pressure at selected pressure points thereby limiting the trunk motion of the person and reminding the person through biofeedback from assuming positions which would injure the lower back. In a more specific aspect, the method comprises the steps of applying to a person to be treated a back support belt formed of a relatively rigid material; and positioning and tightening the belt on said person to increase the intra-abdominal pressure wherein anteriorly said belt applies pressure to the sternal half of the tenth rib and the anterior portion of the iliac crest to restrict excessive forward bending, laterally the belt extends distally from the inferior border of the lateral portion of the tenth rib to the iliac crest to slightly limit lateral trunk motions occurring in the thoraco lumbar and lumbar areas wherein the pressure from said belt along the inferior border of the tenth rib and the superior border of the iliac crest acts to remind the subject of allowable and safe limits of lateral flexion and rotation, and posteriorly the edges of the belt extend distally from the thoraco lumbar joint to the fifth lumbar joint to limit excessive extension of the lumbar spine and decrease lordosis and wherein pressure areas of the inferior edge of the dorsal portion of the twelfth rib and sacral iliac line of the ilium serve as a reminder to the person when excessive extension of the spine is attempted.

DESCRIPTION OF THE PREFERRED EMBODIMENT

Figure 1:
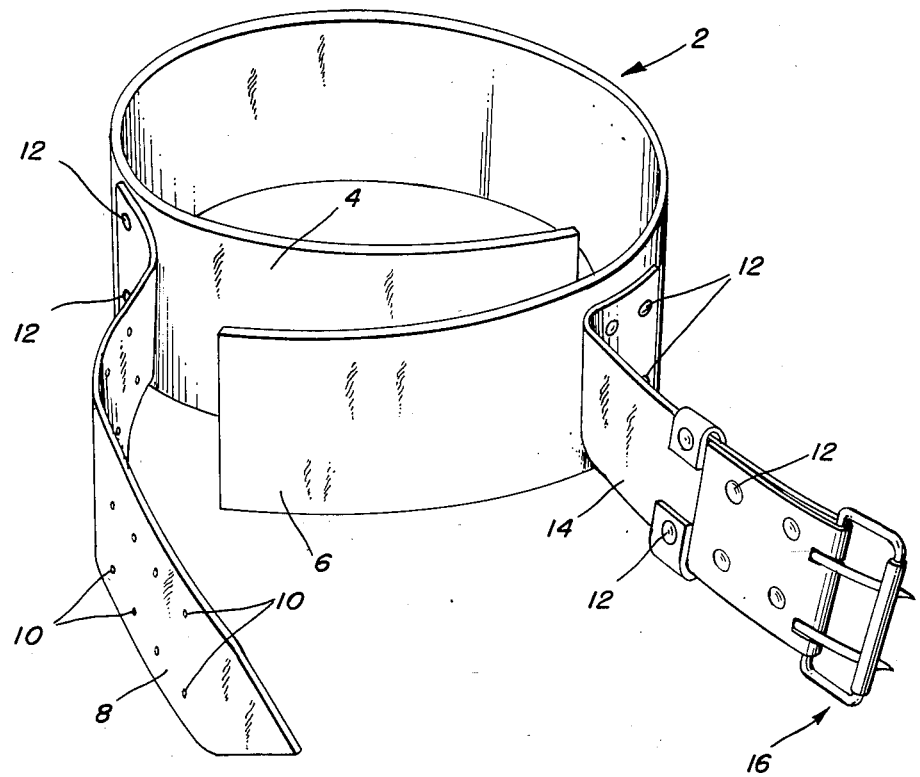
FIG. 1 is a front perspective view of an unfastened back support belt.
Figure 2:
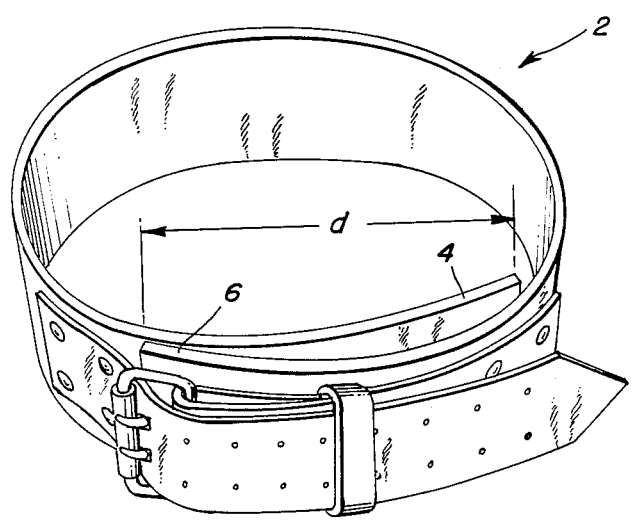
FIG. 2 is a front perspective view of the back support belt fastened to the smallest size.

As shown in FIGS. 1 and 2, the back support belt is formed of an elongate tubular support band 2 which is preferably leather having a thickness of 6 mm or a material which has similar rigidity, stiffness and flexibility characteristics. The elongate support band has a first longitudinal end portion or flap 4 and a second longitudinal end portion or flap 6. In use, these flaps overlap and press against the abdomen of the wearer. Either the first or the second flap can be arranged adjacent to the wearer. The end flaps are held in place and are pressed against the wearer by a first tightening strap 8 of a leather material having a thickness of about 2 mm which contains a plurality of small openings 10 therein and a second tightening strap 14 having a buckle 16 which can be adjustably connected with the first tightening strap 8. The second strap 14 is also formed of a leather material of approximately 2 mm thickness. Other fasteners or connecting means such as Velcro strips, etc. can be used to hold the two overlapping longitudinal end flaps in position and to press the longitudinal end straps against the abdomen of the wearer. The first and second tightening straps are connected with the support band by a plurality of rivets 12. The point of connection of the tightening straps to the respective ends of the elongate support band is preferably 6 to 10 inches from the corresponding longitudinal end of the support band. By connecting the tightening straps in such a manner, either the first or the second longitudinal end portion can be placed against the abdomen of the wearer.

As shown in FIG. 2, the longitudinal end portions of the support band overlap a distance d which is between 5 and 11 inches, preferably 6 and 10 inches.

Figure 3:
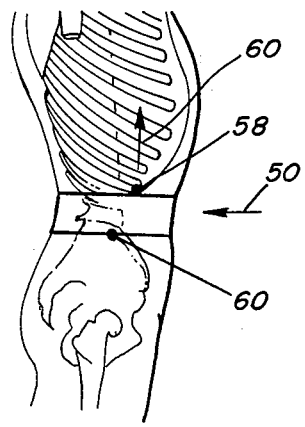
FIG. 3 is a side view of the belt being worn by a subject illustrating various skeletal pressure points.
Figure 4:
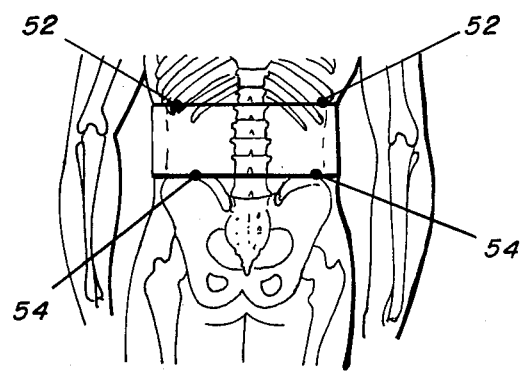
FIG. 4 is a front view of the belt being worn by a subject illustrating skeletal pressure points.
Figure 5:
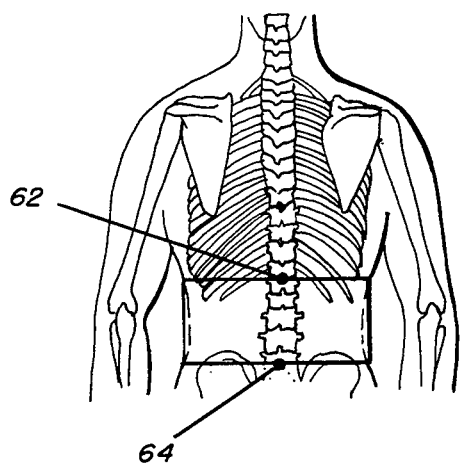
FIG. 5 is a back view of the belt being worn by a subject illustrating skeletal pressure points.

The size of the support belt is selected based upon the height and other body measurements of the wearer. As shown in FIGS. 3-5, the belt assists weak abdominal muscles, particularly the rectus abdominis, and provides a posteriorly directed force in the direction of the arrow 50 to increase intra-abdominal pressure which has been shown to give longitudinal support to the spine and help control excessive lordosis of the lumbar spine. The belt applies pressure at the sternal half of the tenth rib 52 and the anterior portion of the iliac crest 54 thereby restricting excessive forward bending and making the user aware of safe limits of trunk motion. Laterally, the edges of the belt band extend distally from the inferior border of the lateral portion of the tenth rib 58 to the iliac crest 60. When the belt is tightened, a medically directed force is provided which may slightly limit lateral trunk motions occurring in the thoraco lumbar and lumbar areas. The pressure areas along the inferior border of the tenth rib and superior border of the iliac crest act as a form of biofeedback reminding the wearer of the allowable safe limits of trunk lateral flexion and rotation. Posteriorly, the edges of the belt band extend distally from about the thoraco lumbar joints 62 to about the fifth lumbar joint 64. This provides for anteriorly directed forces which may limit excessive extension of the lumbar spine and thereby decrease lordosis. The pressure areas of the inferior edge of the dorsal portion of the tenth rib in the sacral iliac line of the ilium serve as reminding feedback when excessive extension of the spine is attempted. Sufficient clearance between the strap and the back is provided so as to allow for reduction of lordosis when the intra-abdominal pressure is increased by tightening the belt. In addition to applying pressure to the abdomen in the direction of the arrow 50, the belt also applies somewhat of an upward pressure on the ribs of the wearer in the direction of the arrow 60 thereby encouraging proper posture in the wearer and also decreasing the pressure between the discs of the lower back.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:
1. A back support belt, comprising:
    an elongate support band which is $3\frac{1}{2}$ to 6 inches wide along the entire length thereof having a first and second longitudinal end, said support band being formed of leather which is 4 to 8 mm thick or being formed of a relatively rigid material having a similar stiffness as said leather; and
    tightening means for tightening said belt around a subject in a position wherein said first and second longitudinal ends of said support band overlap between 6 to 10 inches and said tightening means applys external pressure to both of said overlapping longitudinal ends of said belt when tightened.
2. The back support belt of claim 1, wherein said elongate support band is formed of a single piece of leather having a substantially uniform width along the entire length thereof.
3. The back support belt of claim 1, wherein said elongate support band has a substantially uniform width along the entire length thereof.
4. The back support belt of claim 1, wherein said tightening means includes a first tightening strap connected with one longitudinal end of said support band and means for adjustably fastening said tightening strap to said elongate support band.
5. The back support belt of claim 4, wherein said tightening means further includes a second tightening strap connected with the other longitudinal end of said support band.
6. The back support belt of claim 5, wherein said second tightening strap contains a buckle having a width smaller than the width of said support band.
7. The back support belt of claim 1, wherein said support band is formed of a strip of leather having a thickness of about 4-8 mm.
8. A back support belt, consisting essentially of:
    a generally straight elongate support band which is $3\frac{1}{2}$ to 6 inches along the entire length thereof and having first and second longitudinal ends, said support band being formed of leather which is 4-8 mm thick or being formed of a relatively stiff material having a similar stiffness as said leather; and
    tightening means for tightening said belt around the midsection of a subject in a position wherein said first and second longitudinal ends of said support band overlap between 6 to 10 inches and further wherein said tightening means urges both of said overlapping longitudinal ends of said belt against the abdomen of a subject when being worn by a subject to increase the intra-abdominal pressure in said subject.
9. The back support belt of claim 8, wherein said elongate support band is formed of a strip of leather having a thickness of about 4-8 mm.
10. The back support belt of claim 8, wherein said elongate support band has a substantially uniform width along the entire length thereof.
11. The back support belt of claim 8, wherein said elongate support band is formed of a strip of leather having a thickness of about 6 mm.

12. A method for limiting the movement of a person and preventing lower back injury, comprising the steps of:
applying to a person to be treated the back support belt of claim 1; and
positioning and tightening said belt on said person to increase the intra-abdominal pressure of said patient.

13. A method for limiting the movement of a person and preventing lower back injury, comprising the steps of:
applying to a person to be treated the back support belt of claim 1; and
positioning and tightening said belt on said person to increase intra-abdominal pressure wherein anteriorly said belt applys pressure to the sternal half of the tenth rib and the anterior portion of the iliac crest to restrict excessive forward bending, laterally said belt extends distally from the inferior border of the lateral portion of the tenth rib to the iliac crest to slightly limit lateral trunk motions occurring in the thoraco lumbar and lumbar areas wherein the pressure from said belt along the inferior border of the tenth rib and the superior border of the iliac crest acts to remind said subject of the allowable and safe limits of lateral flexion and rotation, and posteriorly the edges of said belt extend distally from the thoraco lumbar joint to the fifth lumbar joint to limit excessive extension of the lumbar spine and decrease lordosis and wherein pressure areas of the inferior edge of the dorsal portion of the twelfth rib and the sacral iliac line of the ilium serve as a reminder to said person when excessive extension of the spine is attempted.

14. The method of claim 12, wherein when said belt is applied to said person a space exists between said support band and the lumbar vertebral spinous processes of said person and when said belt is tightened said intra-abdominal pressure presses against the spine of said person to reduce the lordosis which is allowable by said space.

15. The method of claim 13, wherein the two longitudinal ends of said belt are overlapped between 6 to 10 inches on the abdomen of said person and both overlapped portions are pressed against the abdomen of said person to increase intra-abdominal pressure.

16. The back support belt of claim 1, wherein the upper and lower edges on the front and lateral portions of said belt are not padded.

17. A back support belt comprising:
a generally straight elongate support band having first and second longitudinal ends which is $3\frac{1}{2}$ to 6 inches wide along the entire length thereof and which is formed of leather which is 4 to 8 mm thick or formed of a material which has similar rigidity characteristics as said leather;
first connecting means attached to said belt at a point of attachment which is 5 to 11 inches from said first longitudinal end of said support band to thereby define a first longitudinal flap extending from said point of attachment to said first longitudinal end; and
second connecting means attached to said second longitudinal end of said support band adapted for connection with said first connecting means, said first and second connecting means being arranged on said support band in a manner such that said first and second connecting means can be connected in a manner such that said first and second longitudinal ends can be overlapped an amount of from 5 to 11 inches and both of said longitudinal ends of said support band apply pressure to the abdomen of a wearer.

18. The back support belt of claim 17, which comprises a first connecting strap having a width less than the width of said belt, a second connecting strap having a width less than the width of said belt and means for adjustably connecting said first and second straps.

19. A back support belt, comprising:
a generally straight elongate support band formed of leather having a thickness of 4 to 8 mm which is $3\frac{1}{2}$ to 6 inches wide along the entire length thereof, said elongate support band having first and second longitudinal ends and wherein the upper edges of the sides of the belt are not padded;
a first strap attached to said belt at a point of attachment which is 5 to 11 inches from said first longitudinal end thereof thereby defining a first longitudinal flap extending from said point of attachment to said first longitudinal end;
a second strap attached to said second longitudinal end of said support band; and
means for adjustably connecting said first and second straps whereby said first longitudinal flap can overlap said second longitudinal end an amount of 5 to 11 inches.

20. The back support belt of claim 19, wherein the lower edges of the sides of the belt are not padded.

21. The back support belt of claim 19, and further comprising an abdominal pad to the stomach side of said first longitudinal flap.

* * * * *